US012377292B2

(12) United States Patent
Liger et al.

(10) Patent No.: US 12,377,292 B2
(45) Date of Patent: Aug. 5, 2025

(54) COLLABORATIVE IRRADIATING DEVICE

(71) Applicant: P M B, Peynier (FR)

(72) Inventors: Philippe Liger, Peynier (FR); Marc Delmas, Bouc Bel Air (FR); Emmanuel Brau, Manosque (FR)

(73) Assignee: THERYQ, Paris (FR)

( * ) Notice: Subject to any disclaimer, the term of this patent is extended or adjusted under 35 U.S.C. 154(b) by 311 days.

(21) Appl. No.: 17/789,192

(22) PCT Filed: Dec. 22, 2020

(86) PCT No.: PCT/FR2020/052603
§ 371 (c)(1),
(2) Date: Jun. 25, 2022

(87) PCT Pub. No.: WO2021/130450
PCT Pub. Date: Jul. 1, 2021

(65) Prior Publication Data
US 2022/0387825 A1      Dec. 8, 2022

(30) Foreign Application Priority Data
Dec. 26, 2019  (FR) ...................................... 1915627

(51) Int. Cl.
*A61N 5/10*        (2006.01)
(52) U.S. Cl.
CPC .... *A61N 5/1083* (2013.01); *A61N 2005/1087* (2013.01); *A61N 2005/1089* (2013.01)
(58) Field of Classification Search
None
See application file for complete search history.

(56) References Cited

U.S. PATENT DOCUMENTS

| 10,071,264 | B2 | 9/2018 | Liger |
| 2012/0035470 | A1 | 2/2012 | Kuduvalli et al. |
| 2016/0183899 | A1 | 6/2016 | Vancamberg et al. |
| 2016/0287905 | A1 * | 10/2016 | Liger .................. A61N 5/1067 |
| 2019/0314645 | A1 * | 10/2019 | Ciresianu ............. A61N 5/1082 |

FOREIGN PATENT DOCUMENTS

| EP | 3071292 B1 | 3/2019 | |
| PL | 218852 B1 * | 2/2015 | |
| WO | WO-2016054256 A1 * | 4/2016 | ............. A61B 10/04 |

OTHER PUBLICATIONS

Marie-Catherine Vozenin et al., "The Advantage of FLASH Radiotherapy Confirmed in Mini-pig and Cat-cancer Patients", Clin Cancer Res., Jan. 1, 2019, pp. 35-42, vol. 25. No. 1.

* cited by examiner

*Primary Examiner* — Andrew Smyth
(74) *Attorney, Agent, or Firm* — NIXON & VANDERHYE

(57) ABSTRACT

An irradiating device, configured for irradiating a target, includes a 6-axis arm, an irradiating system positioned at the free end of the 6-axis arm, a manipulating handle, at least one load sensor placed between the manipulating handle and the 6-axis arm, and a control-actuation unit. The irradiating system includes a microwave frequency source and a radiation source supplied by the microwave frequency source. The manipulating handle is fastened to the radiation source. The control-actuation unit is configured to receive information from the load sensor and control the 6-axis arm according to the information received from the load sensor.

14 Claims, 3 Drawing Sheets

COLLABORATIVE IRRADIATING DEVICE

RELATED APPLICATIONS

This application is a § 371 application of PCT/FR2020/052603 filed Dec. 22, 2020, which claims priority from French Patent Application No. 1915627 filed Dec. 26, 2019, each of which is incorporated herein by reference in its entirety.

FIELD OF THE INVENTION

The present application concerns a collaborative irradiating device, for example for radiotherapy.

Such a device is also called a "cobot".

BACKGROUND OF THE INVENTION

External, or intraoperative, radiotherapy (IORT: intraoperative radiotherapy), is a loco-regional method of treating cancers. It is, with surgery, the most frequent treatment for cancers and may lead to clear remission by itself. It may be used alone or associated with surgery and chemotherapy. Its indications are linked to the type of tumor, to its location, its stage and to the general state of the target (in general a region to treat in the patient). In certain cases, it presents the advantage of being carried out on an outpatient basis on account of the fact that the sessions may be of short duration and the secondary effects less than those of a chemotherapy.

For this, the radiotherapy uses ionizing radiation (X-rays, electrons, protons, etc.) to destroy the cancer cells by affecting their capacity to reproduce. The irradiation is directed to destroying all the tumor cells while sparing healthy peripheral tissues.

However, for certain types of cancer, treatment by X-rays presents the difficulty that the tumor may be located very close to parts of organs which it is preferable to avoid irradiating.

Furthermore, it has become apparent that delivering very high doses over very short periods (typically less than one second) is much less harmful for healthy tissues than delivering the same dose, or even a lower dose, in a longer time (i.e. several seconds, or even several minutes, for a conventional treatment mode). This phenomenon is described for example in the paper "The Advantage of FLASH Radiotherapy Confirmed in Mini-pig and Cat-cancer Patients", Marie-Catherine Vozenin et al., Clin Cancer Res 2018, American Association for Cancer Research.

Such a treatment mode is in particular designated "flash radiotherapy".

Flash radiotherapy thus makes it possible to produce the same therapeutic effects as conventional radiotherapy while limiting possible undesirable side effects.

Furthermore, flash radiotherapy may make it possible to avoid removing the tumor in advance, which is particularly convenient if the tumor is inoperable (for example when a tumor is located in the vicinity of a patient's carotid or pancreas since there is too great a risk of affecting the nervous system).

Flash radiotherapy thus makes it possible to treat a greater variety of tumors, in particular tumors that are ordinarily inoperable (for example by conventional means, for example by a scalpel).

It is also necessary to accurately deliver, measure and/or control the high doses of ionizing radiation administered in very brief periods. The impacts of improper control of dose and/or of the dose rate absorbed by the target may lead to destruction of healthy cells, tissues or organs and the secondary effects which ensue therefrom may in certain cases, have detrimental effects on organs at risk.

Document EP3071292 for example describes an irradiating device using ionizing radiation for radiotherapy and/or radiobiology enabling the flash mode to be used. The device thus comprises an ion or electron beam linear accelerator, commonly called "LINAC", and control and actuation electronics which enables general stoppage of the emission of ionizing radiation when the dose prescribed by the operator has been reached, and more particularly an irradiating device using ionizing radiation configured to deliver, in accurate and controlled manner, a dose of ionizing radiation of at least 0.25 Gy (gray), preferably 10 Gy, in an energy range comprised between 1 MeV and 50 MeV, over very brief instants, that is to say for example less than 100 ms, possibly less than 1 ms, possibly less than 100 µs, possibly less than 0.1 µs. It also relates to an irradiating device using ionizing radiation provided with a power pulse control system capable of producing an energy particle beam adjustable within a range comprised between 1 MeV and 50 MeV, pulsed at a desired frequency (f) with an adjustable pulse duration (d) and capable of delivering an absorbed dose rate of at least 250 Gy/s, possibly 500 Gy/s or even of at least 1000 Gy/s in a field of exposure from a few $cm^2$ (square centimeters) to 10 $cm^2$. In practice, the beam emitted by the radiation source (LINAC for example) must be applied at a particular angle and particular distance relative to the target.

There are conventional radiotherapy devices which for example comprise a 6-axis robot one end of which bears a LINAC.

Generally, a practitioner positions an applicator on the target (on the patient, or partly in the patient according to the case) and holds it by hand. Next, another practitioner moves the device in order for the source of radiation at an exit of the LINAC to be connected to the applicator. Next, everyone leaves the room where the patient is located and the radiation is activated to perform the treatment. For this, a man-machine interface (MMI) is generally organized in the room referred to as "control room" which is located next to a room referred to as "operation room" in which the patient and the irradiating device are located. The operation room is then equipped with a radiation protection bunker.

Document US2019/0314645 for example describes a radiotherapy device comprising a 6-axis robot configured to align a treatment head having a fixed applicator to an operation table.

The procedure for manipulating the irradiating device is thus very long and delicate since the LINAC must be oriented according to particular prescriptions relative to the target (and thus relative to the applicator) while the device is very heavy and difficult to manipulate.

Therefore, automated devices have been developed, for example devices capable of detecting a target, or for example that are guided by an external system, or that are remotely controlled (for example via a joystick).

However, not only is such a device difficult to remotely control, but it is generally more pleasant and practical for a practitioner to be able to directly manipulate the irradiating device.

Furthermore, to perform flash radiotherapy, it is necessary to have greater power available than with conventional radiotherapy, giving rise all the more to weight in the irradiating device, which counters the ease of manipulating the device.

OBJECT AND SUMMARY OF THE INVENTION

The object of the present invention is thus to provide an irradiating device using ionizing radiation, in particular for radiotherapy and/or radiobiology, overcoming at least partly the aforementioned drawbacks.

To that end, according to a first aspect there is provided an irradiating device configured to irradiate a target in flash or conventional mode, comprising:
- A 6-axis robot comprising a base and a 6-axis arm of which a first end is attached to the base and a second end is designated free end;
- An irradiating system, comprising a microwave frequency source and a radiation source supplied by the microwave frequency source, the irradiating system being positioned at the free end of the 6-axis arm;
- A manipulating handle, joined to the radiation source;
- At least one load sensor placed between the manipulating handle and the 6-axis arm, or possibly between the manipulating handle and the radiation source; and
- A control-actuation unit configured to receive information from the load sensor and control the 6-axis arm according to the information received from the load sensor.

The at least one load sensor converts the load to which it is subjected into electrical signal.

The electrical signal measurement sent by the load sensor is converted into radiation source movement and orientation control.

A load submitted to a sensor in a direction X is converted into a command for movement in the direction X with an acceleration and a velocity which depend upon the level of the load, that is to say on the amplitude of the electrical signal sent by the load sensor in the direction X.

When two load sensors positioned on a axis of direction Y are subjected to loads of different levels in a same direction X, the difference in level constitutes a couple applied according to a direction Z perpendicular to the plane which contains the axis of direction Y, on which are positioned the load sensors, and the direction X.

This level difference in loads results in a difference in amplitude of signals sent by the load sensors in the direction X.

This amplitude difference in electrical signals is then converted into a command for rotation around an axis for direction Z with an acceleration and a velocity which depend on the difference in level of the loads, that is to say the difference in the amplitudes of the electrical signals sent by the two load sensors in the direction X.

The load sensors thus enable feedback control of the irradiating device such that the irradiating device then forms a collaborative robot, or "cobot", the manipulation of which is assisted.

The device may for example be manipulated by a single person whereas at least two persons were generally required to manipulate a conventional device.

According to the invention, the sensors thus enable interpretation of the intentions for movement by the practitioner and compensate for the stresses between the different interfaces which provide better ergonomics for the device, i.e. make it easier to manipulate.

Thus, for example, the irradiating device is configured to adopt at least a use configuration, in which the 6-axis arm is in an extended position, and a configuration for storage and/or movement in which the 6-axis arm is then in a folded position. In this configuration, the compactness of the irradiating device is then better, which makes it more easily movable if needed.

The irradiating device, and more particularly the irradiating system, comprises the manipulating handle.

The at least one load sensor is placed between the manipulating handle and the 6-axis arm.

However, if it is placed between the 6-axis arm and the irradiating system, the loads transmitted are very great since the irradiating system, which is positioned at the free end of the 6-axis arm, weighs approximately 150 kg.

Thus, in an example embodiment that is particularly practical to reduce these loads, the at least one load sensor is placed between the manipulating handle and the radiation source.

In a favored example embodiment, the irradiating device comprises at least two, possibly three, load sensors.

The manipulating handle comprises for example a fixed wheel or loop; it may nevertheless comprise any part of the device able to transmit loads to the at least one load sensor in order to move and orientate the radiation source.

The wheel may for example surround an exit of the radiation source so as not to obstruct the radiation emitted and thereby provide a grip for the practitioner whatever his position.

In an example embodiment, the irradiating device in particular makes it possible to perform flash therapy.

A device capable of performing flash therapy is detailed in the aforementioned document EP3071292 for example.

In particular here, in order to perform flash therapy, it is necessary to have a maximum of radiation power. To maximize the available power, the microwave frequency source has thus been positioned as close as possible to the radiation source, which makes it possible to minimize the electromagnetic power losses between the microwave frequency source and the particle beam accelerator cavity, providing the useful radiation.

By virtue of the invention, it is thus possible to produce a device able to deliver more radiation power, therefore capable of performing flash therapy, but which is not more bulky than the known prior art systems.

Furthermore, the person skilled in the art was prejudiced against positioning both a microwave frequency source and a radiation source, of LINAC type, in the same assembly fastened at an arm end due to the high corresponding weight.

As a matter of fact, in the prior devices, the microwave frequency source was generally used as a counterweight for the radiation source; such a disposition facilitated the balancing of the device but led to high losses in microwave frequency electromagnetic power.

However, to position both the microwave frequency source and the radiation source at the end of the arm has in fact proved possible thanks to the 6-axis arms henceforth available.

On the other hand, it is however preferable to limit the excess weight which may be induced by other components at the end of the arm.

The microwave frequency source here designates a source of electromagnetic waves configured to produce an electromagnetic field of frequency at least 300 MHz, preferably in the S-band of electromagnetic frequencies (i.e. between 2 GHz and 4 GHz) or in the C-band (i.e. between 4 GHz and 8 GHz) or for instance in the X-band (i.e. between 8 GHz and 12 GHz).

The irradiating system is for example configured to emit ionizing radiation and deliver at least one dose of that ionizing radiation, of at least 20 Gy, for example 30 Gy, in less than 100 ms, or possibly less than 1 µs.

According to a favored example embodiment, the radiation source comprises a linear accelerator of electrons referred to as LINAC.

This irradiating system is for example configured to emit ionizing radiation by pulses at a repetition frequency (f)

comprised between 10 Hz and 1 kHz, each pulse having a duration (d) comprised between 10 ns and 100 μs for example.

For example, the irradiating system is configured here to deliver a dose per pulse comprised between 1 Gy and 10 Gy.

In an advantageous example embodiment, possibly for example the radiation source, comprises an ultra-fast sensor, for example a solid-state sensor of silicon carbide or diamond, or a sensor with one or more ionizing chambers, or for instance a current transformer (i.e. of the Bergoz brand for example) if the ionizing radiation is radiation of charged particles, such as electrons or protons.

An ultra-fast sensor here is preferably positioned at the exit of the source of the ionizing radiation beam so as to be passed through by the entirety of the radiation stream from the radiation source.

In this way, the ultra-fast sensor is configured to monitor the radiation dose delivered to a target.

An ultra-fast sensor here is a sensor configured to detect a dose of ionizing radiation in less than 0.01 ns and at dose throughputs of at least 0.01 Gy/s, or even 25 Gy/s, or even 50 Gy/s, or preferably even 250 Gy/s, still another possibility being 500 Gy/s or even 1000 Gy/s.

Such as sensor makes it possible to detect a dose of ionizing radiation that is produced in less than 0.01 ns and at dose throughputs of at least 0.01 Gy/s, or even 25 Gy/s, or even 50 Gy/s, or preferably even 250 Gy/s, still another possibility being 500 Gy/s or even 1000 Gy/s.

In an advantageous example embodiment, the irradiating system comprises a casing in which are placed the microwave frequency source and the radiation source, and on which is fastened the manipulating handle; the at least one load sensor being interposed between the manipulating handle and a surface of the casing.

According to an advantageous option, the base further comprises a stabilizing system configured to compensate for a weight induced by the irradiating system positioned at the free end of the 6-axis arm.

The stabilizing system makes it possible to better compensate for a lever arm or cantilever effect due to the positioning of the radiation system and to give greater reach to the 6-axis arm and avoid tipping of the device.

The stabilizing system comprises for example at least one leg-stand.

According to an advantageous aspect, the stabilizing system further comprises a retractable board configured to take an extended position and a retracted position, the board in extended position then facing opposite the radiation.

Such a board for example makes it possible to avoid the radiation passing through a partitioning structure, for example a floor of the room in which the device is located, or any other object that it is preferable to protect from the radiation.

The base may also comprise, for example, a power source for the ionizing radiation source in order for the device to be able to operate in flash mode.

The power source here designates a high voltage electrical source.

According to another option, the base may also comprise an omnidirectional movement system, for example comprising wheels.

The irradiating device may thus be moved in any direction.

In an advantageous example embodiment, the wheels of the base are holonomic. The movement system thus enables the rotational movement of the irradiating device around any axis perpendicular to the surface of the ground on which the device moves. In particular, the device itself can thus rotate. The movement system of the base, in particular such wheels, also enables translational movement of the irradiating device on the ground in any direction without rotation. The holonomic wheels of the base also enable simultaneous rotational and translational movements of the irradiating device. The advantage of such a movement system is the maneuverability of the irradiating device to get into position in a cluttered or restricted space.

In an example embodiment, the irradiating device, optionally for example the irradiating system further comprises an applicator configured to be fastened at an exit of the radiation source.

The use of a 6-axis arm enables the applicator to be positioned and oriented as desired by the practitioner, which enables any target to be reached by the radiation, whatever the position of the target in the patient.

The applicator here forms an interface between the target and the radiation source.

It may be held by the practitioner facing the target while the radiation source carried by the 6-axis arm is brought by another practitioner to be connected to the applicator.

The approach may be manual and assisted by the 6-axis arm motorized and controlled by the forces applied on the load sensor or sensors, in particular by the manipulating handle.

In another example embodiment, the final approach and the alignment of the axis of the radiation source with the axis of the applicator may be automated. For this, the irradiating device comprises for example a connection system comprising at least one location reference for the applicator and a sensor, preferably fastened to the robot, for example to the radiation source.

The sensor makes it possible to locate the applicator relative to the radiation source. The location of the applicator relative to the radiation source in turn makes it possible to control the movements of the 6-axis arm carrying the radiation source so as to align the latter with the axis of the applicator to dock it and automatically fasten it without specific action by an operator.

Alternatively, especially for a non-invasive case, the applicator may be fastened to the radiation source, possibly manually and/or indirectly via the load sensor or sensors.

Thus, the applicator is not only aligned with the radiation source, without direct contact, but is fastened at an exit from the radiation source. The practitioner can thus move, orientate and position the radiation source and applicator group on the target to treat by manipulating the applicator, or even any other component configured to move the radiation source and transmit forces to the load sensor or sensors.

Thus, in an example embodiment, the manipulating handle comprises the applicator.

The at least one load sensor is thus interposed here between the applicator and a surface of the irradiating system casing. Due to this, the applicator can apply forces to at least one load sensor so as to serve as a manipulating handle.

When, for example, the manipulating handle comprises at the same time an applicator and a wheel, the practitioner can apply a high torque by holding the handle with one hand the applicator with the other, enabling him or her to easily manipulate the irradiating system, and in particular to position a free end of the applicator more easily and with better accuracy in relation to the target.

BRIEF DESCRIPTION OF THE DRAWINGS

The invention, according to an example embodiment, will be well understood and its advantages will be clearer on reading the following detailed description, given by way of illustrative example that is in no way limiting, with reference to the accompanying drawings in which.

Identical parts represented in the aforementioned figures are identified by identical numerical references.

DETAILED DESCRIPTION OF THE EMBODIMENTS

Figure 1:
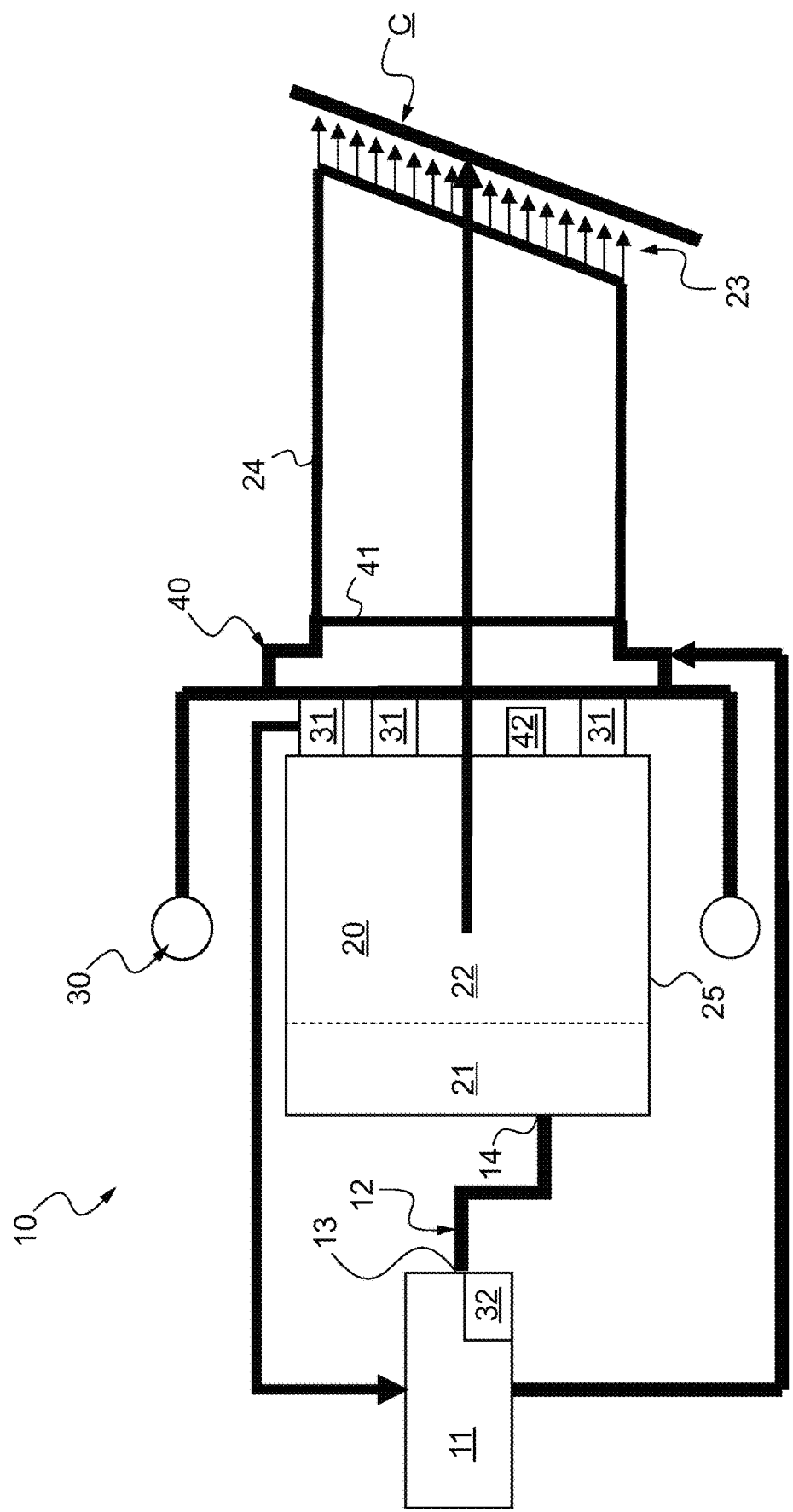
FIG. 1 is a diagrammatic representation of an irradiating device according to an example embodiment of the invention.

An irradiating device 10 for irradiating a target C is shown diagrammatically in FIG. 1.

The irradiating device 10 mainly comprises a base 11 and a 6-axis arm 12.

The 6-axis arm 12 comprises a first end 13 by which it is fastened to the base 11 and a second end 14 is referred to as free end.

At the first end 13, the 6-axis arm 12 comprises for example an interface configured to fasten the arm to the base 11.

Here, at its free end 14, the 6-axis arm 12 is provided with an irradiating system 20.

The irradiating system 20 is rigidly fastened here to the free end 14 of the 6-axis arm 12.

The irradiating system 20 here mainly comprises a microwave frequency source 21 and a radiation source 22 supplied by the microwave frequency source 21.

The radiation source 22 here is configured to emit a beam 23, for example an electron beam.

The radiation source 22 is for example a LINAC.

The irradiating system 20, possibly the radiation source 22, also comprises an ultra-fast sensor (not shown) configured to monitor an amount of radiation dose delivered to a target.

The ultra-fast sensor is preferably positioned here at an exit of the ionizing radiation source so as to be passed through by the entirety of the radiation stream.

An ultra-fast sensor here is a sensor configured to detect a dose of ionizing radiation in less than 0.01 ns and at dose throughputs of at least 0.01 Gy/s, or even 25 Gy/s, or even 50 Gy/s, or preferably even 250 Gy/s, still another possibility being 500 Gy/s or even 1000 Gy/s.

Such as sensor makes it possible to detect a dose of ionizing radiation that is produced in less than 0.01 ns and at dose throughputs of at least 0.01 Gy/s, or even 25 Gy/s, or even 50 Gy/s, or preferably even 250 Gy/s, still another possibility being 500 Gy/s or even 1000 Gy/s.

The ultra-fast sensor may be a solid state sensor of silicon carbide or diamond, or a sensor with one or more ionizing chambers, or for instance a current transformer if the ionizing radiation is radiation of charged particles, such as electrons or protons.

In the present example embodiment, the irradiating system 20 comprises a casing 25. The microwave frequency source 21 and the radiation source 22 are confined here within the casing 25.

The irradiating device 10 further comprises a manipulating handle 30, which is preferably joined to the radiation source 22.

In particular here, the manipulating handle 30 is fastened to the casing 25.

The manipulating handle 30 comprises for example a loop forming a handle.

In order to make the irradiating device collaborative, the irradiating device 10 comprises load sensors 31, here three load sensors 31.

The load sensors 31 are placed here between the manipulating handle 30 and the radiation source 22, and more specifically here, the load sensors 31 are interposed between the manipulating handle 30 and a surface of the casing 25.

In a preferred example embodiment, the three sensors are disposed in a triangle.

Thus, when a practitioner manipulates the manipulating handle 30 the load sensors 31 sense the loads transmitted to the manipulating handle 30 and send a corresponding signal to a control-actuation unit 32.

Thus, the control-actuation unit 32 controls the 6-axis arm to collaborate with the positioning and with the orientation of the radiation source 22 relative to the target C.

The control-actuation unit 32 is represented here in the base 11.

The control-actuation unit 32 is thus configured to receive information from the load sensors and control the 6-axis arm according to the information received from the load sensors.

The irradiating system 20 also here comprises an applicator 24 positioned at an exit of the radiation source 22. Here, the applicator is rigidly fastened to part of the handle 30 by means of a fastening system 40 configured to fasten the applicator at an exit of the radiation source 22.

The applicator 24 is for example a tube, for example a perspex tube.

In an example embodiment, the fastening system 40 also comprises a docking system 41 and a position sensor 42.

The position sensor 42 is for example placed on the irradiating system 20 and preferably on the radiation source 22.

If the applicator 24 is held by a practitioner in position facing opposite the target C without yet being connected in any way at an exit from the radiation source 22, the fastening system 40 is configured to actuate the 6-axis arm 12 so as to fasten the radiation source 22 to the applicator 24, in the position in which it is held.

The position sensor 42 detects the position of the applicator 24, sends corresponding information to the control-actuation unit 32 which controls the 6-axis arm 12 to position the radiation source 22 and which activates the fastening system 40 so as to fasten the applicator 24 in its position held by the practitioner at an exit from the radiation source 22.

The base 11 thus comprises at least control-actuation unit 32.

Figure 2:
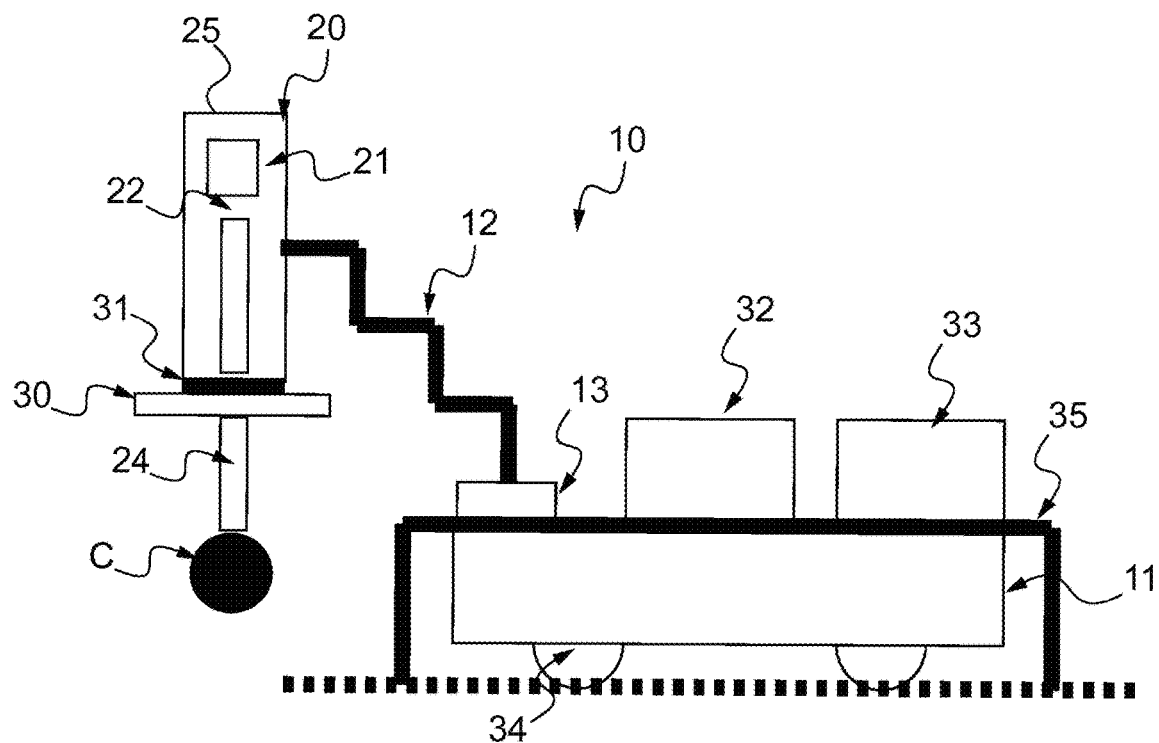
FIG. 2 is a diagram of a flash irradiating device according to an example embodiment of the invention.

As shown in FIG. 2, the base 11 may also comprise, for example, a power source 33 for the ionizing radiation source in order for the device to be able to operate in flash mode.

The base 11 may also comprise an omnidirectional movement system 34, comprising for example wheels, which are for example holonomic. The irradiating device 10 can thus be simultaneously moved translationally and rotationally in any direction.

Lastly, the base 11 preferably comprises a stabilizing system 35.

The stabilizing system 35 is configured to immobilize, in stable manner, the irradiating device 10.

The stabilizing system 35 for example comprises legstands, and possibly also a retractable board (not shown) configured to have an extended position and a retracted position, the board in extended position then being located facing opposite the radiation.

The presence of such a board thus makes it possible to use the irradiating device at different locations while limiting the risk of the radiation passing through a partition structure present facing opposite the radiation.

Figure 3:
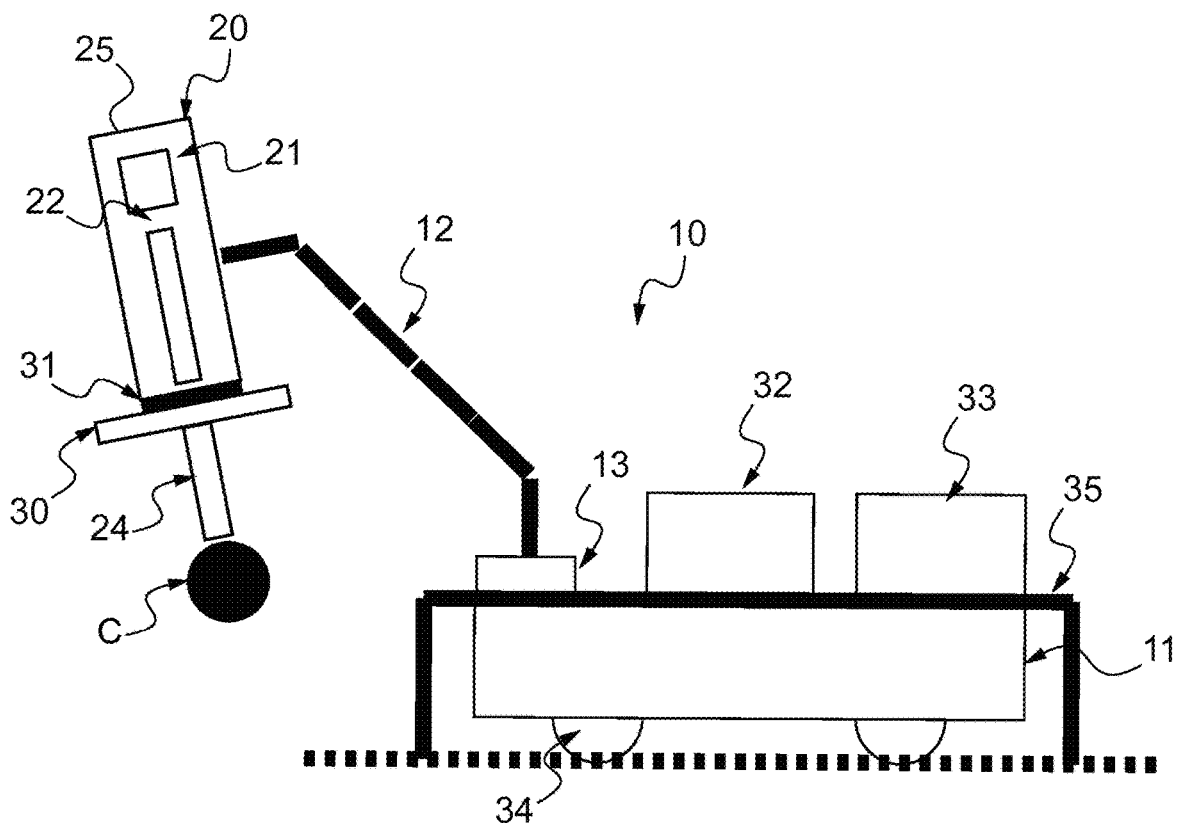
FIG. 3 shows the device of FIG. 2 with the arm extended.
Figure 4:
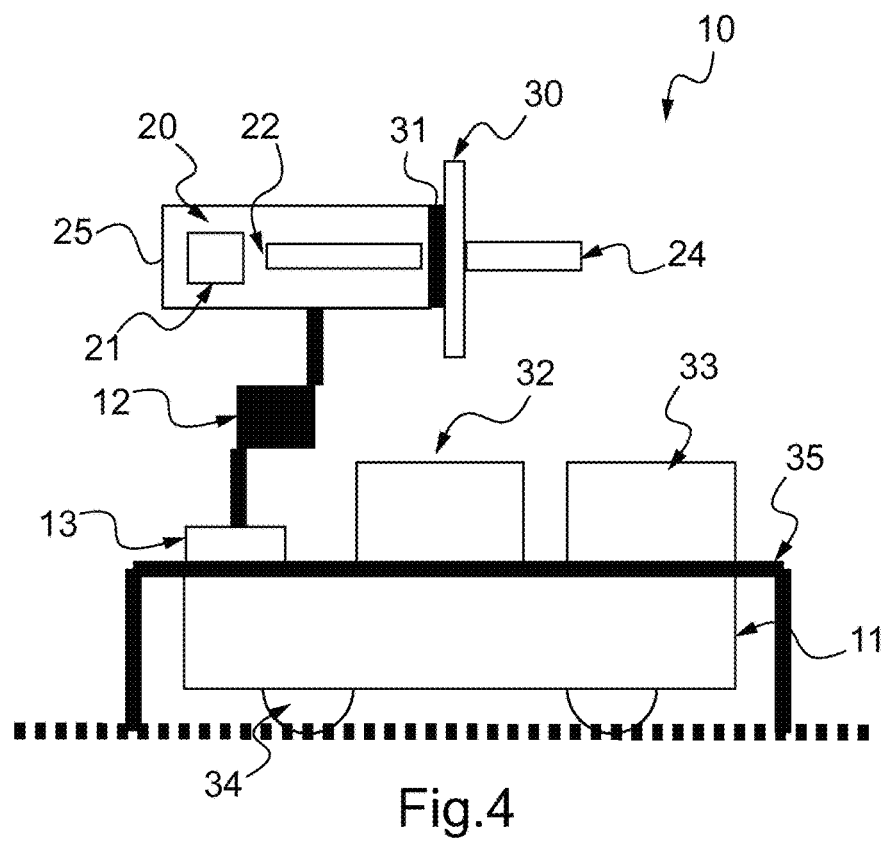
FIG. 4 shows the device of FIG. 3 with the arm folded, in order to move and stow it.

By way of illustration, FIGS. 2 to 4 shows the irradiating device 10 in different configurations.

In FIG. 2, the irradiating device 10 is in a configuration of use in which the applicator is positioned facing the target C. The 6-axis arm 12 is thus in an extended position.

In FIG. 3, the irradiating device 10 is also in a configuration of use in which the applicator is positioned facing opposite the target C, but the 6-axis arm 12 is then in a deployed extended position, that is to say at maximum span. As a matter of fact, the irradiating device according to the invention makes it possible to reach more varied regions to treat on a target C.

In FIG. 4, the irradiating device 10 is in a configuration for storage and/or movement. The 6-axis arm 12 is thus in a folded position. The compactness of the irradiating device is then better, which makes it more easily movable.

Figure 5:
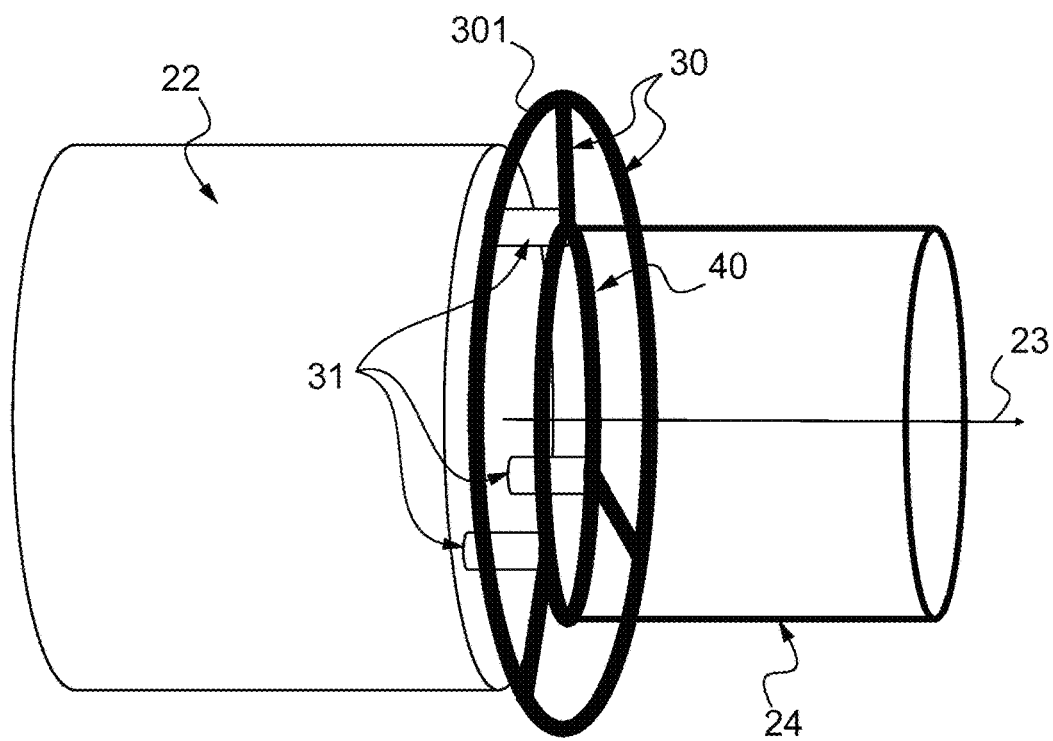
FIG. 5 shows an example of geometry and interfaces of the ionizing radiation source, load sensors, the manipulating handle and the applicator.

FIG. 5 illustrates in more detail an example embodiment of the manipulating handle 30 and of load sensors 31.

In this example, the applicator 24 is rigidly fastened, joined, to part of the manipulating handle 30, for example by means of the fastening system 40, which is rigid, between the applicator 24 and the part of the manipulating handle 30.

Thus, the applicator forms part of the manipulating handle 30. A practitioner can thus move and position the irradiating system (20) by holding the applicator 24.

The part of the manipulating handle 30 is formed by a wheel 301 here.

The wheel 301 case thus surround an exit of the radiation source 22 so as not to obstruct the radiation emitted.

The wheel 301 is rigidly connected to the radiation source 22, and to a connecting interface between the wheel 301 and the radiation source 22, three load sensors 31 are positioned, in a triangle, here in a same plane.

The load sensors 31 are thus configured to send signals corresponding to the loads applied via the handle to the control-actuation unit 32, and the control-actuation unit 32 is configured to generate corresponding signals to control the movements of the 6-axis arm 12, in order to collaborate with the positioning and with the orientation of the radiation source 22 relative to the target C to aim at.

The invention claimed is:

1. An irradiating device configured to deliver a radiation dose to a target, comprising:
a 6-axis robot comprising a base and a 6-axis arm, the 6-axis arm comprising a first end attached to the base and a second end designated as a free end;
an irradiating system, comprising a microwave frequency source and a radiation source supplied by the microwave frequency source, the irradiating system being positioned at the free end of the 6-axis arm;
a manipulating handle, joined to the radiation source, comprising an applicator configured to be fastened at an output of the radiation source;
at least one load sensor arranged between and physically connecting the manipulating handle to the 6-axis arm; and
a controller-actuator configured to receive information from said at least one load sensor and to control the 6-axis arm according to an information received from said at least one load sensor.

2. The device of claim 1, wherein the 6-axis arm comprises an extended position and a folded position for storage and movement.

3. The device of claim 1, wherein the radiation source comprises a LINAC.

4. The device of claim 1, wherein the irradiating system comprises a casing in which are placed the microwave frequency source and the radiation source, the manipulating handle being fastened on the casing, and said at least one load sensor being interposed between the manipulating handle and a surface of the casing.

5. The device of claim 1, wherein the irradiating system comprises at least two load sensors.

6. The device of claim 1, wherein said at least one load sensor is placed between the manipulating handle and the radiation source.

7. The device of claim 1, wherein the base further comprises a stabilizing system configured to compensate a weight induced by the irradiating system positioned at the free end of the 6-axis arm.

8. The device of claim 7, wherein the stabilizing system comprises a retractable board configured to take an extended position and a retracted position, the retractable board facing opposite the radiation source when in the extended position.

9. The device of claim 1, wherein the irradiating system is configured to emit a ionizing radiation and deliver a dose of the ionizing radiation of at least 20 Gy in less than 100 ms.

10. The device of claim 1, wherein the manipulating handle comprises a wheel surrounding the exit of the radiation source.

11. The device of claim 1, wherein the base comprises a power source for supplying the radiation source, the power source being a voltage source.

12. The device of claim 1, wherein the base comprises an omnidirectional movement system.

13. The device of claim 1, wherein the irradiating system comprises an ultra-fast sensor configured to monitor the radiation dose delivered to the target.

14. The device of claim 13, wherein the ultra-fast sensor is configured to detect the radiation dose in less than 0.01 ns and at a throughputs of at least 0.01 Gy/s.

* * * * *